United States Patent [19]

Soltis et al.

[11] Patent Number: 5,362,651
[45] Date of Patent: Nov. 8, 1994

[54] CARBON MONOXIDE SELECTIVE SENSOR AND METHOD OF ITS USE

[75] Inventors: Richard E. Soltis, Redford; Eleftherios M. Logothetis, Birmingham; Jacobus H. Visser, Belleville, all of Mich.

[73] Assignee: Ford Motor Company, Dearborn, Mich.

[21] Appl. No.: 156,666

[22] Filed: Nov. 22, 1993

Related U.S. Application Data

[63] Continuation of Ser. No. 919,312, Jul. 27, 1992, abandoned.

[51] Int. Cl.$^5$ .............................................. G01N 27/16
[52] U.S. Cl. .................................. 436/134; 422/98; 422/83; 422/88; 422/90; 436/137
[58] Field of Search ............... 422/94, 98, , 83, 88, 422/90; 436/134, 137, 151; 505/1, 136, 252; 156/646

[56] References Cited

U.S. PATENT DOCUMENTS

| | | | |
|---|---|---|---|
| 3,970,431 | 7/1976 | Wise | 422/98 |
| 4,251,225 | 2/1981 | Handa et al. | 422/98 |
| 4,397,888 | 8/1983 | Yannopoulos et al. | 422/94 |
| 4,504,599 | 3/1985 | Sasaki et al. | 502/202 |
| 4,543,273 | 9/1985 | Handa et al. | 422/94 |
| 4,587,104 | 5/1986 | Yannopoulos | 422/94 |
| 4,792,433 | 12/1988 | Katsura et al. | 422/98 |
| 4,978,646 | 12/1990 | Bardhan et al. | 501/136 |
| 5,015,616 | 5/1991 | Sekido et al. | 422/94 |
| 5,017,264 | 5/1991 | Yamazaki et al. | 156/646 |
| 5,037,761 | 8/1991 | Barnett et al. | 422/94 |
| 5,051,396 | 9/1991 | Yamazaki | 505/1 |
| 5,082,789 | 1/1992 | Morrison et al. | 422/94 |
| 5,106,824 | 4/1992 | Uno et al. | 505/1 |
| 5,157,016 | 10/1992 | Yamaguchi et al. | 505/1 |
| 5,168,068 | 12/1992 | Yanagisawa et al. | 436/134 |

FOREIGN PATENT DOCUMENTS

| | | | |
|---|---|---|---|
| 2753035 | 6/1978 | Germany | 422/94 |
| 1438193 | 7/1972 | Japan | 422/94 |
| 90256 | 7/1981 | Japan | 422/94 |
| 153246 | 11/1981 | Japan | 422/98 |
| 102142 | 6/1983 | Japan | 422/98 |
| 1155746 | 7/1986 | Japan | 422/94 |

OTHER PUBLICATIONS

Yanmaz et al. "Direct current zoning (DCZ) and direct current annealing (DCA) of meet-cast BiPbSrCaCuO rods"; J. Alloy, Compd. (13 Jul. 1992), vol. 185(2) pp. 311–320.

*Primary Examiner*—David A. Redding
*Attorney, Agent, or Firm*—Lorraine S. Melotik; Roger L. May

[57] ABSTRACT

A sensor which is selective to carbon monoxide relative to other reducing gases includes a Bi—Sr—Ca—Cu—O system metal oxide element.

8 Claims, 2 Drawing Sheets

RELATIVE SENSITIVITY TO VARIOUS GASES

RELATIVE SENSITIVITY TO VARIOUS GASES

CARBON MONOXIDE
SENSITIVITY AT VARIOUS TEMPERATURES

CARBON MONOXIDE SELECTIVE SENSOR AND METHOD OF ITS USE

This application is a continuation, of application Ser. No. 07/919,312, filed Jul. 27, 1992 now abandoned.

FIELD OF THE INVENTION

This invention relates generally to carbon monoxide selective sensors. More particularly, the invention is directed to a sensor material which selectively detects carbon monoxide in a mixture of reducing gases.

BACKGROUND OF THE INVENTION

Simple and inexpensive sensors that can selectively detect carbon monoxide in the presence of other gases, especially other reducing gases, are needed for controlling the exhaust gas emissions of internal combustion engines as well as for other health and safety applications. Metal oxide resistive type sensors and calorimetric-type sensors are presently available for detecting carbon monoxide. However, these sensors are non-selective with respect to other reducing gases. This restriction severely limits the usefulness of these types of sensors for motor vehicle engine applications, because the exhaust gases from such engines contain a wide variety of hydrocarbons and other interfering species along with the carbon monoxide.

It is well-known that the electrical conductivity of many metal oxide sensors may be modified by the adsorption or reaction of gases on their surfaces. This characteristic may be used for the purpose of detecting such gases. Thus, a gas sensor may be prepared, comprising a metal oxide having a surface which can be exposed to an atmosphere containing the particular gas or gases to which the device is sensitive. The sensor typically includes a pair of spaced-apart electrodes in electrical communication with the metal oxide. The amount of electric current which may be passed between the electrodes at a constant applied voltage will be dependent upon the conductivity of the metal oxide. Such devices are typically operable over a particular temperature range and a specific detectable gas concentration range.

U.S. Pat. No. 4,587,104 to Yannopoulos discloses a device for detecting and measuring the amount of carbon monoxide and hydrogen contained in a mixture of reducing gases. The device comprises a bismuth molybdate ($Bi_2O_3 \cdot 3MoO_3$) based semiconductor oxide element having two platinum wire electrodes. The electrical conductivity of the device varies in response to the concentration of carbon monoxide and hydrogen in a mixture of reducing gases, but the device is not selective to carbon monoxide alone.

It would be desirable to prepare a sensor which is selective to carbon monoxide. The desired sensor should additionally be useful over a wide range of carbon monoxide concentrations and temperatures.

SUMMARY OF THE INVENTION

Accordant with the present invention, there surprisingly has been discovered a device for detecting the presence of carbon monoxide. The device comprises:

A) a metal oxide element having the general formula:

wherein M is a metal ion selected from the group consisting of silicon, germanium, tin, antimony, lead, bismuth, and mixtures thereof, M' is a metal ion selected from the group consisting of strontium, barium, and mixtures thereof, a is from about 1.5 to about 2, b is from 0 to about 0.5, c is from about 1 to about 2, d is from 0 to about 2, e is from 0 to about 0.5, f is from about 1 to about 3, and g is from about 6 to about 12; and B) a pair of spaced-apart electrodes in electrical communication with the metal oxide element.

Moreover, a novel process for measuring the concentration of carbon monoxide in a mixture of gases has been discovered. The process comprises the steps of:

A) providing a sensor, comprising:

i) a metal oxide element having the general formula:

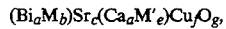

wherein M is a metal ion selected from the group consisting of silicon, germanium, tin, antimony, lead, bismuth, and mixtures thereof, M' is a metal ion selected from the group consisting of strontium, barium, and mixtures thereof, a is from about 1.5 to about 2, b is from 0 to about 0.5, c is from about 1 to about 2, d is from 0 to about 2, e is from 0 to about 0.5, f is from about 1 to about 3, and g is from about 6 to about 12; and ii) a pair of spaced-apart electrodes in electrical communication with the metal oxide element;

B) exposing the sensor to an atmosphere containing carbon monoxide; and

C) measuring a flow of electrical current between the electrodes.

The carbon monoxide sensors of the present invention are particularly useful for monitoring the concentration of carbon monoxide in an internal combustion exhaust gas stream and providing feedback to more efficiently control the combustion process.

BRIEF DESCRIPTION OF THE DRAWINGS

The novel features that are considered characteristic of the invention are set forth with particularity in the appended Claims. The invention will best be understood, however, by reference to the accompanying description of specific embodiments when read in conjunction with the attendant drawings in which:

DETAILED DESCRIPTION OF THE PREFERRED EMBODIMENT

Figure 3:
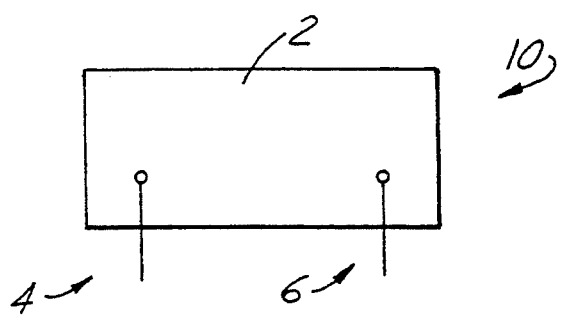
FIG. 3 is a schematic view of an embodiment of the inventive sensor.

The present invention is directed to a sensor which can selectively detect and measure carbon monoxide in the presence of other gases, including reducing species such as hydrogen, propane, methane, etc.; and to a process for measuring the concentration of carbon monoxide utilizing the novel sensor. As shown in FIG. 3, the sensor 10 comprises a metal oxide element 2, shown in a bulk material embodiment, and a pair of spaced-apart electrodes 4 and 6 which are in electrical communication with the metal oxide element 2. The sensor is based on a metal oxide material whose electrical conductivity varies as a result of exposure to the carbon monoxide at an elevated temperature. An increased concentration of carbon monoxide results in a decrease in the electrical conductivity of the novel metal oxide sensor. The metal oxide reverts to its original, standard electrical conductivity upon its removal from the carbon monoxide-containing atmosphere, thereby indicating that the conductivity-modifying processes involved are reversible.

The material from which the sensor element is made is a metal oxide having the general formula:

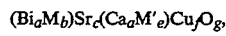

$$(Bi_aM_b)Sr_c(Ca_dM'_e)Cu_fO_g,$$

wherein M is a metal ion selected from the group consisting of silicon, germanium, tin, antimony, lead, bismuth, and mixtures thereof, M' is a metal ion selected from the group consisting of strontium, barium, and mixtures thereof, a is from about 1.5 to about 2, b is from 0 to about 0.5, c is from about 1 to about 2, d is from 0 to about 2, e is from 0 to about 0.5, f is from about 1 to about 3, and g is from about 6 to about 12. A preferred unsubstituted metal oxide is $Bi_2Sr_2CaCu_2O_8$. A preferred substituted BSCCO includes metal ions selected from the group consisting of lead, tin, and mixtures thereof.

The metal oxide useful for preparing the carbon monoxide sensor of the present invention is well-known in the art as a superconducting material, generally designated by the term "BSCCO." The BSCCO system has several distinct phases, as well as substituted variations thereof. For example, $Bi_2Sr_2CaCu_2O_8$ is a well-known superconducting material having a Tc of about 85K, while $Bi_2Sr_2Ca_2Cu_3O_{10}$ becomes superconductive below about 110K. It is also well-known to substitute lead for some of the bismuth ions to form $Bi_{2-x}Pb_xSr_2Ca_2Cu_3O_{10}$, wherein x is from greater than zero to about 0.5. It must be noted, however, that a great deal of uncertainty still exists with respect to the actual structures of the various substituted and unsubstituted BSCCO systems.

While not wishing to be bound by an particular theory regarding the mechanism by which BSCCO acts as a carbon monoxide sensor, it is believed that the mechanism is analogous to the operation of tin oxide as a sensor for reducing gases. Tin oxide is an n-type semiconductor metal oxide. When tin oxide is exposed to air, oxygen is adsorbed onto its surface as a negatively charged species, by taking electrons from the conduction band of the solid. In the absence of reducing gases in the air, a certain concentration of the negatively charged oxygen species resides on the surface of the tin oxide, while the concentration of electrons within the solid attains a certain value $n_o$. By contrast, when reducing molecules are present along with the air which contacts the tin oxide element, the reducing molecules interact with adsorbed surface oxygen, removing some of these adsorbed oxygen species and returning the associated electrons to the conduction band of the solid tin oxide. At steady state reducing conditions, the electron concentration within the element n is greater than $n_o$, resulting in a lower electrical resistance, either because the conductivity is greater or because the intergrain resistance decreases.

It is believed that BSCCO behaves in a similar manner. BSCCO is a p-type metal oxide, which can be metalic or semiconducting, wherein the charge carriers are holes instead of electrons. It is theorized that, when BSCCO is exposed to air, oxygen is adsorbed as a negatively charged species by taking an electron from the valence band of the BSCCO, which establishes an equilibrium hole concentration $p_o$ within the element. By contrast, when carbon monoxide is present along with the air which contacts the BSCCO, it (and, to a lesser extent, other reducing molecules) interacts with the adsorbed surface oxygen, to remove some of the oxygen species and return the associated electrons to the valence band of the BSCCO element. This results in a decreased hole concentration within the element. At steady state reducing conditions, the hole concentration p is less than $p_o$, resulting in a greater electrical resistance for the BSCCO element. The mechanism for the selective nature of the BSCCO to carbon monoxide relative to other reducing gases, however, is not understood.

The metal oxide of the present invention may be formed into a sensor element by conventional methods. Generally, powders of the binary oxides or carbonates of the appropriate elements initially are mixed together. For example, $Bi_2O_3$, $SrCO_3$, $CaCO_3$, CuO, and optionally compounds such as PbO, $SnO_2$, or $SiO_2$, may be mixed together as a precursor powder for the preparation of unsubstituted or substituted BSCCO. The powder precursor is then calcined at a temperature in the range from about 750° C. to about 900° C. for a number of hours. After calcination, the resultant material is ground to a fine powder which is subjected to additional heat treatment steps. The ultimately reacted powder is then sintered at a temperature in the range from about 800° C. to about 900° C. for a period of time ranging up to about 300 hours to form a metal oxide element.

Alternatively, the unreacted precursor powder may be hot-pressed to form a pellet, which is then used as a target in a magnetically enhanced rf triode sputtering process to produce an unsubstituted or substituted BSCCO film element on a substrate such as MgO.

Methods for preparing substituted and unsubstituted BSCCO bulk and film elements are more fully set forth in Soltis, R. E. et al., "Properties Of BiSrCaCuO Films Prepared by RF Triode Sputtering," Physica C. 162-164 (1989) 649-650, Elsevier Science Publishers B.V., North Holland, and in U.S. Pat. No. 5,087,607 to Strom et al., which are incorporated herein in their entireties by reference thereto.

The methods for preparing BSCCO described hereinabove are generally discloses in terms of their broadest application to the practice of the present invention. Occasionally, the methods as described may not be applicable to each compound included within the disclosed scope. Those compounds for which this occurs will readily be recognizable to those ordinarily skilled in the art. In all such cases, either the methods may be successfully performed by conventional modifications known to those ordinarily skilled in the art, e.g., by substituting alternative conventional chemical reagents, by routine modifications of reaction conditions, etc., or other methods for preparing BSCCO which are otherwise conventional will be applicable to the practice of the present invention.

A pair of spaced-apart electrodes are attached to the metal oxide element by conventional techniques. The electrodes may be made of any materials known to be useful for conducting electrical current such as, for example, platinum wires. The electrodes conveniently may be attached to the bulk metal oxide element by embedding the electrodes in the powder mixture during the final sintering process. Alternatively, the electrodes may be attached to the film element by placing the electrodes on the film substrate then depositing the film of metal oxide thereover. The electrodes are in electrical communication with the metal oxide element, so that an electrical current may be passed through one of the electrodes, thence through the element, and finally through the other electrode. The metal oxide elements prepared according to the present invention have large surface areas which may be exposed to an atmosphere containing the carbon monoxide.

The process for measuring the concentration of carbon monoxide in a mixture of gases, according to the present invention, comprises exposing the sensor to the gas mixture and measuring a flow of electrical current between the electrodes. The electrical conductivity is dependent upon the concentration of the carbon monoxide in the gas mixture. The electrical conductivity of the element will decrease from its standard value at a zero concentration of carbon monoxide, to a lower value at a higher concentration of carbon monoxide.

In operation, the sensor electrodes are connected to a conventional electrical circuit adapted to pass an electrical current therethrough, including means for measuring the electrical conductivity of the sensor element. Any change in this current due to changes in the conductivity of the metal oxide element caused by a change in carbon monoxide concentration, can then be detected and, if desired, measured.

Figure 1:
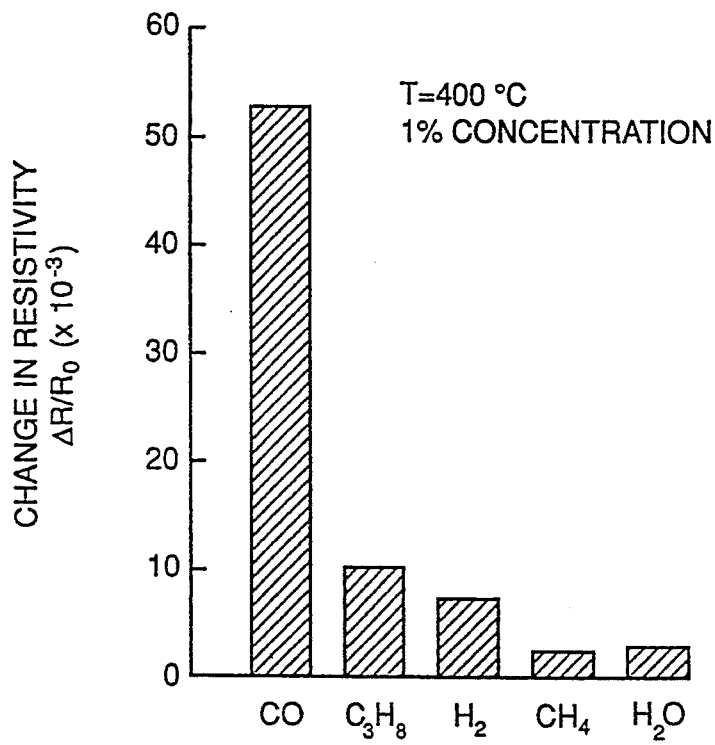
FIG. 1 is a graph illustrating the relative sensitivity of the inventive sensor to various gases.
Figure 2:
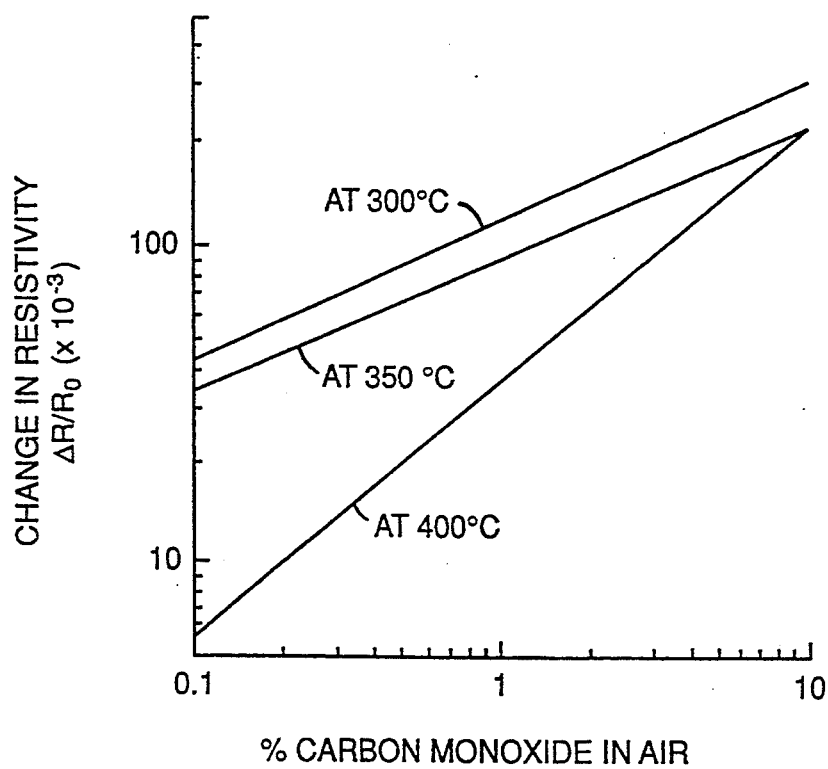
FIG. 2 is a graph illustrating the carbon monoxide sensitivity of the inventive sensor at various temperatures.
Figure 4:
FIG. 4 is a schematic view illustrating the inventive sensor in an automotive vehicle for detecting carbon monoxide in the exhaust gases from the vehicle's internal combustion engine.

FIG. 1 illustrates the relative sensitivity of the metal oxide sensor of the present invention. The sensor is selective to carbon monoxide, relative to other conventional reducing gases. FIG. 2 illustrates the sensitivity of the metal oxide sensor of the present invention at various temperatures. It will be readily apparent to one ordinarily skilled in the art that the inventive sensor would be particularly useful for monitoring the combustion off gases from a residential furnace or industrial boiler for health and safety considerations, or for monitoring internal combustion engine exhaust for improved engine feedback control as shown in FIG. 4 for an automotive vehicle. The inventive sensor may operate over a wide range of temperatures from about 200° C. to about 650° C. Preferably, the sensor is used to measure carbon monoxide over a temperature range from about 300° C. to about 450° C. Moreover, the useful range of carbon monoxide concentrations over which the inventive device will operate varies widely from greater than zero to about 65%. Preferably, the sensor is most sensitive at carbon monoxide concentrations from greater than zero to about 5%.

The results described may be repeated with similar success by substituting the generically or specifically described reactants and/or reaction conditions for those recited herein. From the foregoing description, one ordinarily skilled in the art can easily as certain the essential characteristics of this invention, and without departing from the spirit and scope thereof, can make various changes and modifications in the invention to adapt it to various usages and conditions.

We claim:

1. A carbon monoxide sensor, comprising:
   A) a metal oxide element constructed so as to be exposed to a gas comprising carbon monoxide, having the general formula:

$(Bi_aM_b)Sr_c(Ca_dM'_e)Cu_fO_gV$ wherein M is a metal ion selected from the group consisting of silicon, germanium, tin, antimony, lead, bismuth, and mixtures thereof, M' is a metal ion selected from the group consisting of strontium, barium, and mixtures thereof, a is from about 1.5 to about 2, b is from 0 to about 0.5, c is from about 1 to about 2, d is from 0 to about 2, e is from 0 to 0.5, f is from about 1 to 3, and g is from about 6 to about 12; and
   B) a pair of spaced-apart electrodes in electrical communication with the metal oxide element.

2. The carbon monoxide sensor according to claim 1, wherein M is a metal ion selected from the group consisting of lead, tin, and mixtures thereof.

3. The carbon monoxide sensor according to claim 1, wherein the metal oxide is $Bi_2Sr_2CaCu_2O_8$.

4. A process for detecting carbon monoxide, comprising the steps of:
   A) providing a sensor, comprising:
      i) a metal oxide element having the general formula:

$(Bi_aM_b)Sr_c(Ca_dM'_e)Cu_fO_gV$ wherein M is a metal ion selected from the group consisting of silicon, germanium, tin, antimony, lead, bismuth, and mixtures thereof, M' is a metal ion selected from the group consisting of strontium, barium, and mixtures thereof, a is from about 1.5 to about 2, b is from 0 to about 0.5, c is from about 1 to about 2, d is from 0 to 2, e is from 0 to about 0.5, f is from about 1 to 3, and g is from about 6 to about 12; and
      ii) a pair of spaced-apart electrodes in electrical communication with the metal oxide element;
   B) exposing the sensor to an atmosphere containing carbon monoxide; and
   C) measuring a flow of electrical current between the electrodes.

5. The process for detecting carbon monoxide according to claim 4, wherein M is a metal ion selected from the group consisting of lead, tin, and mixtures thereof.

6. The process for detecting carbon monoxide according to claim 4, wherein the semiconducting metal oxide is $Bi_2Sr_2CaCu_2O_8$.

7. A device for detecting carbon monoxide including a carbon monoxide sensor, the improvement wherein the sensor comprises:
   A) a metal oxide element constructed so as to be exposed to a gas-comprising carbon monoxide, having the general formula:

$(Bi_aM_b)Sr_c(Ca_dM'_3)Cu_fO_g,$ wherein M is a metal ion selected from the group consisting of silicon, germanium, tin, antimony, lead, bismuth, and mixtures thereof, M' is a metal ion selected from the group consisting of strontium, barium, and mixtures thereof, a is from about 1.5 to about 2, b is from 0 to about 0.5, c is from about 1 to about 2, d is from 0 to 2, e is from 0 to about 0.5, f is from about 1 to 3, and g is from about 6 to about 12; and
   B) a pair of spaced-apart electrodes in electrical communication with the metal oxide element.

8. The process for detecting carbon monoxide according to claim 4, wherein the sensor is provided in an automobile for detecting carbon monoxide in the exhaust gases from the internal combustion engine.

* * * * *